US012508018B2

(12) United States Patent
Song et al.

(10) Patent No.: US 12,508,018 B2
(45) Date of Patent: Dec. 30, 2025

(54) BIODEGRADABLE THREAD MANUFACTURING APPARATUS AND METHOD, AND BIODEGRADABLE THREAD THEREOF

(71) Applicant: HYUNDAEMEDITECH CO., LTD., Wonju-si (KR)

(72) Inventors: Mi Hee Song, Wonju-si (KR); Chul Park, Yongin-si (KR)

(73) Assignee: HYUNDAEMEDITECH CO., LTD., Wonju-si (KR)

( * ) Notice: Subject to any disclaimer, the term of this patent is extended or adjusted under 35 U.S.C. 154(b) by 548 days.

(21) Appl. No.: 17/907,251

(22) PCT Filed: Sep. 5, 2022

(86) PCT No.: PCT/KR2022/013237
§ 371 (c)(1),
(2) Date: Sep. 23, 2022

(87) PCT Pub. No.: WO2023/167381
PCT Pub. Date: Sep. 7, 2023

(65) Prior Publication Data

US 2024/0293116 A1 Sep. 5, 2024

(30) Foreign Application Priority Data

Mar. 4, 2022 (KR) ........................ 10-2022-0027919

(51) Int. Cl.
*A61B 17/06* (2006.01)
*D02G 3/44* (2006.01)

(52) U.S. Cl.
CPC ......... *A61B 17/06166* (2013.01); *D02G 3/44* (2013.01); *A61B 2017/06052* (2013.01); *A61B 2017/06176* (2013.01)

(58) Field of Classification Search
CPC .... A61B 17/06166; A61B 2017/06052; A61B 2017/06176; D02G 3/44; D02J 3/02
(Continued)

(56) References Cited

U.S. PATENT DOCUMENTS 8,216,273 B1 * 7/2012 Goraltchouk .... A61B 17/06166 606/228
2004/0060409 A1 * 4/2004 Leung .................... A61B 17/04 83/522.14
(Continued)

FOREIGN PATENT DOCUMENTS

KR 10-2004-0041593 A 5/2004
KR 10-1692467 B1 1/2017
(Continued)

OTHER PUBLICATIONS

International Search Report for PCT/KR2022/013237 by Korean Intellectual Property Office dated Dec. 12, 2022.

*Primary Examiner* — Kankindi Rwego
(74) *Attorney, Agent, or Firm* — BROADVIEW IP LAW, PC

(57) ABSTRACT

The present invention relates to biodegradable thread manufacturing apparatus including: a thread feeding unit for feeding a biodegradable thread; and a cog formation unit for forming cogs on the outer peripheral surface of the biodegradable thread fed from the thread feeding unit, wherein the cog formation unit may include a multi-bladed part for forming the cogs each having two or more peaks whose end portions are separated from each other through a one-time operation thereof.

2 Claims, 9 Drawing Sheets

(58) Field of Classification Search
USPC .................................... 28/295; 606/228, 230
See application file for complete search history.

(56) References Cited

U.S. PATENT DOCUMENTS

| | | | | |
|---|---|---|---|---|
| 2004/0226427 | A1 | 11/2004 | Trull et al. | |
| 2011/0288583 | A1* | 11/2011 | Goraltchouk .......... | A61B 17/08 606/228 |

FOREIGN PATENT DOCUMENTS

| | | | | |
|---|---|---|---|---|
| KR | 10-2018-0024466 | A | 3/2018 | |
| KR | 10-2020-0043134 | A | 4/2020 | |

* cited by examiner (b)

(a)

(b)

BIODEGRADABLE THREAD MANUFACTURING APPARATUS AND METHOD, AND BIODEGRADABLE THREAD THEREOF

CROSS-REFERENCE TO RELATED APPLICATIONS

This application is a National Phase Entry Application of PCT Application No. PCT/KR2022/013237 filed on Sep. 5, 2022, which claims priority to Korean Patent Application No. 10-2022-0027919 filed on Mar. 4, 2022, in Korean Intellectual Property Office, the entire contents of which are hereby incorporated by reference in its entirety.

TECHNICAL FIELD

The present invention relates to a biodegradable thread manufacturing apparatus and method and a biodegradable thread thereof, and more specifically, to biodegradable thread manufacturing apparatus and method and a multi-bladed part mounted on the same apparatus that are capable of improving the production efficiency of a biodegradable thread and surgery effectiveness using the biodegradable thread.

BACKGROUND ART

Recently, face plastic surgery has been changed from face lifting using a scalpel to face lifting using a melting thread, not using any scalpel. The thread lifting, which is used to remove wrinkles from the face, the lower jaw, the neck, and the like, is conducted by inserting a biodegradable thread (suture) into the skin to pull and remove wrinkles.

In specific, the lifting surgery is performed by inserting the biodegradable thread into a needle-shaped cannula 1 (See FIG. 1), inserting the cannula 1 into, for example, the cheek of the face, and drawing the cannula 1 to the outside while pressurizing the biodegradable thread inserted into the face.

The lifting surgery provides excellent wrinkle removal effectiveness and is performed in a simple manner. Further, since the lifting surgery has fewer side effects than drug treatments such as Botox injection, it is widely used.

The biodegradable thread is made of materials such as polyglycolic acid, polydioxanone, polyglyconate, and the like. In specific, polydioxanone is used for biomedical applications, especially for surgical sutures, which is completely dissolved within six months after implantation to thus cause no foreign body reactions.

Further, as shown in FIG. 1, a biodegradable thread 10 has thorn-type cogs 11 formed diagonally on the outer peripheral surface thereof to obtain more excellent skin lifting effectiveness. Through a biodegradable thread manufacturing apparatus, in this case, the cogs 11 are formed on the biodegradable thread 10 in longitudinal and circumferential directions of the biodegradable thread 10.

In specific, conventional biodegradable thread manufacturing apparatuses make the biodegradable thread with the cogs by means of a blade part, and while the biodegradable thread 10 turns axially around at a given place, in this case, the cogs are formed on the biodegradable thread 10 by means of the blade part, thereby manufacturing the biodegradable thread 10 as shown in FIG. 1.

However, the conventional biodegradable thread manufacturing apparatuses are configured to have a single-bladed part to thus cause a process of forming the cogs on the biodegradable thread to become relatively long, thereby having low biodegradable thread productivity.

Therefore, there is a need to develop a new biodegradable thread manufacturing apparatus and a new blade part mounted thereon that are capable of forming cogs on a biodegradable thread in a more rapid and simpler manner than the conventional biodegradable thread manufacturing apparatuses.

DISCLOSURE

Technical Problem

Accordingly, the present invention has been made to solve the above-mentioned problems, and it is an object of the present invention to provide a biodegradable thread manufacturing apparatus and method and a multi-bladed part mounted on the same apparatus that are capable of allowing a cog having two or more separated peaks to be formed on a biodegradable thread through a one-time operation of the multi-bladed part of a cog formation unit, thereby improving the production efficiency of the biodegradable thread and further allowing the coupling force of the biodegradable thread with skin tissues to be enhanced if the biodegradable thread including the cogs each having the peaks formed to a set shape is applied to a patient's skin, thereby obtaining great effectiveness in the patient's skin lifting.

The technical problems to be achieved through the present invention are not limited as mentioned above, and other technical problems not mentioned herein will be obviously understood by one of ordinary skill in the art through the following description.

Technical Solution

To accomplish the above-mentioned objects, according to an aspect of the present invention, there is provided a biodegradable thread manufacturing apparatus including: a thread feeding unit for feeding a biodegradable thread; and a cog formation unit for forming cogs on the outer peripheral surface of the biodegradable thread fed from the thread feeding unit, wherein the cog formation unit may include a multi-bladed part for forming the cogs each having two or more peaks whose end portions are separated from each other through a one-time operation thereof.

According to the present invention, the multi-bladed part may include a first blade member and a second blade member located above the first blade member so as to form the cogs each having the two or more peaks on the biodegradable thread in a longitudinal direction of the biodegradable thread through the one-time operation thereof.

To accomplish the above-mentioned objects, according to another aspect of the present invention, there is provided a multi-bladed part of a cog formation unit for forming cogs on the outer peripheral surface of a biodegradable thread, which is disposed on a biodegradable thread manufacturing apparatus, including two or more blade members for forming a cog having two or more peaks whose end portions are separated from each other through a one-time operation thereof.

To accomplish the above-mentioned objects, according to another aspect of the present invention, there is provided a biodegradable thread manufacturing method including the steps of: feeding a biodegradable thread through a thread feeding unit; and forming a cog having two or more peaks whose end portions are separated from each other on the outer peripheral surface of the biodegradable thread through a one-time operation of a multi-bladed part of a cog formation unit.

To accomplish the above-mentioned objects, according to another aspect of the present invention, there is provided a biodegradable thread having a plurality of cogs formed on the outer peripheral surface, wherein the cogs each having two or more peaks whose end portions are separated from each other, and the peaks are separated left and right based on a longitudinal direction of the biodegradable thread.

Advantageous Effects

According to the present invention, the biodegradable thread manufacturing apparatus is configured to allow the cog having two or more separated peaks to be formed on the biodegradable thread through the one-time operation of the multi-bladed part of the cog formation unit, thereby improving the production efficiency of the biodegradable thread, and further, if the biodegradable thread including the cogs each having the peaks formed to the set shape is applied to the patient's skin, the coupling force of the biodegradable thread with the skin tissues is enhanced, thereby obtaining great effectiveness in the skin lifting.

MODE FOR INVENTION

Figure 1:
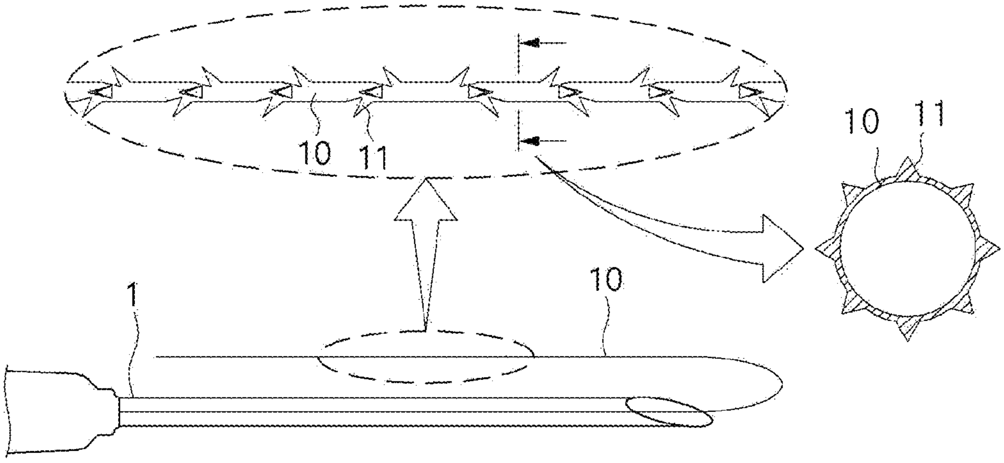
FIG. 1 is an exemplary view showing a state in which a biodegradable thread with cogs is inserted into a cannula.

Objects, characteristics and advantages of the present invention will be more clearly understood from the detailed description as will be described below and the attached drawings. Before the present invention is disclosed and described, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. In the description, the corresponding parts in the embodiments of the present invention are indicated by corresponding reference numerals.

Hereinafter, embodiments of the present invention will be explained in detail with reference to the attached drawings.

Figure 2:
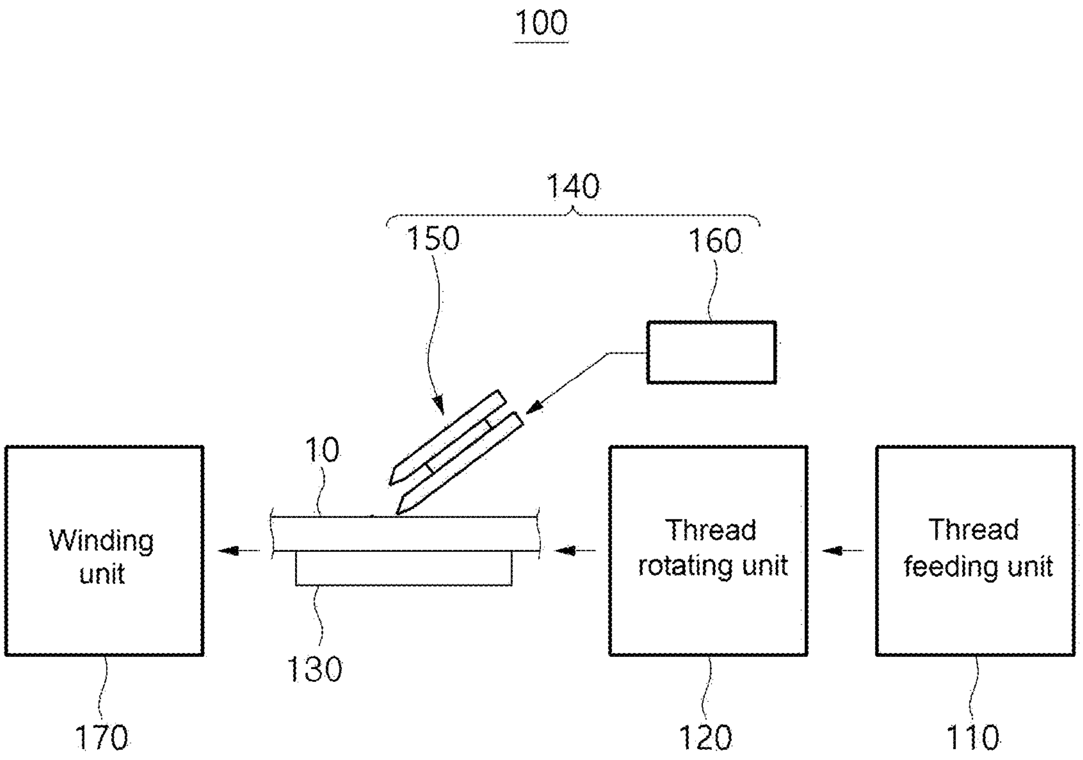
FIG. 2 is a block diagram showing a biodegradable thread manufacturing apparatus according to the present invention.
Figure 3:
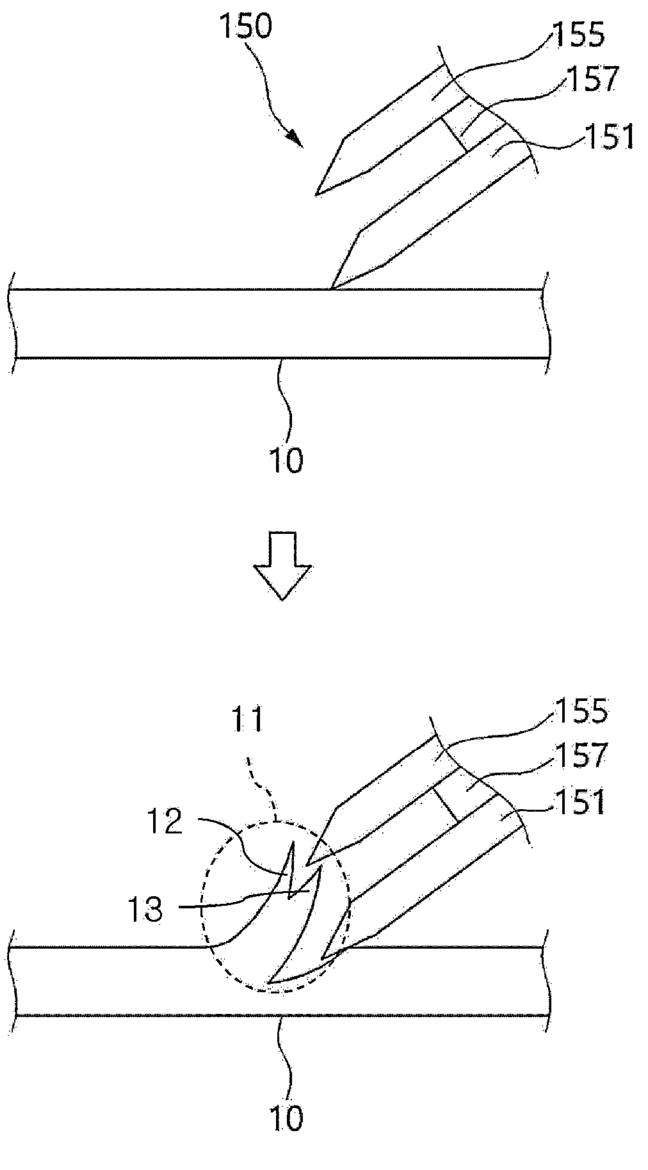
FIG. 3 is a side view showing a state in which cogs are formed on a biodegradable thread by means of a multi-bladed part of a cog formation unit of FIG. 2.

FIG. 2 is a block diagram showing a biodegradable thread manufacturing apparatus according to the present invention, and FIG. 3 is a side view showing a state in which cogs are formed on a biodegradable thread by means of a multi-bladed part of a cog formation unit of FIG. 2.

As shown, a biodegradable thread manufacturing apparatus 100 for manufacturing a biodegradable thread 10 with cogs 11 formed thereon according to the present invention includes a thread feeding unit 110 for feeding the biodegradable thread 10, a thread rotating unit 120 for rotating the biodegradable thread 10 fed from the thread feeding unit 110 by a set angle, a cog formation unit 140 having a multi-bladed part 150 adapted to form the cogs 11 on the outer peripheral surface of the biodegradable thread 10, and a winding unit 170 for winding the biodegradable thread 10 with the cogs 11 formed by the cog formation unit 140.

According to the present invention, the multi-bladed part 150 of the cog formation unit 140 is configured to form a cog having two or more peaks 12 and 13 whose ends are separated from each other through a one-time operation.

Under the above-mentioned configuration, through the one-time operation of the cog formation unit 140, the cog 11 having the two peaks 12 and 13 is formed on the biodegradable thread 10, thereby improving the production efficiency of the biodegradable thread 10, and further, if the biodegradable thread 10, which includes the cogs 11 each having the peaks 12 and 13 formed to a set shape, is applied to a patient's skin, a coupling force of the biodegradable thread 10 with the patient's skin tissues is enhanced, thereby obtaining great effectiveness in the patient's skin lifting.

Now, explanations of the respective units of the biodegradable thread manufacturing apparatus 100 according to the present invention will be given. Even though the tread feeding unit 110 is not shown in detail in configuration, first, the thread feeding unit 110 is a roll type unit around which the biodegradable thread 10 is wound to feed the biodegradable thread 10 as a raw material at a set speed as it rotates.

In this case, the biodegradable thread 10 according to the present invention is a polydioxanone (PDO) thread that is biodegradable if a given time passes after it has been inserted into the skin, and the biodegradable thread 10 has the thorn-shaped cogs 11 as will be discussed later, which increase the coupling force with the skin tissues.

In specific, for example, if the biodegradable thread 10 is inserted into the skin tissues of the cheeks of the face through the cannula 1 (See FIG. 1), a degree of tightness of the biodegradable thread 10 with the skin tissues is improved by means of the cogs 11 formed on the biodegradable thread 10 to thus obtain great effectiveness in the skin lifting.

However, the biodegradable thread 10 is not limited to the above-mentioned material, and accordingly, the biodegradable thread 10 may be formed of materials such as a polyglycolic acid thread, a polyglyconate thread, and the like. Further, the shape of each cog 11 may be varied freely.

Even though the thread rotating unit 120 is not shown in detail in configuration, it rotates the biodegradable thread 10 fed from the thread feeding unit 110 by the set angle to allow the cogs as set shapes to be formed on the biodegradable thread 10 through the cog formation unit 140.

For example, the thread rotation unit 120 rotates the biodegradable thread 10 by 45° at set time intervals to allow the cogs 11 to be formed on the outer peripheral surface of the biodegradable thread 10 in a spiral direction of the biodegradable thread 10 at the angle of 45°, as shown in FIG. 1.

However, the rotating angle of the biodegradable thread 10 made by the thread rotation unit 120 is not limited to the above-mentioned angle, and for example, the thread rotation unit 120 may rotate the biodegradable thread 10 by 90°, 180°, and the like.

As schematically shown in FIG. 2, the cog formation unit 140 includes the multi-bladed part 150 for forming the cog 11 having the two or more peaks 12 and 13 on the outer peripheral surface of the biodegradable thread 10 through the one-time operation and a blade operating member 160 for operating the multi-bladed part 150.

According to the present invention, the cog formation unit 140 is configured to allow the cog 11 having the two or more peaks 12 and 13 whose ends are separated from each other to be formed on the biodegradable thread 10 placed on a cog formation stage 130 through the one-time operation.

The multi-bladed part 150 operates with the driving force supplied from the blade operating member 160, and the blade operating member 160 is connected to the multi-bladed part 150 by means of, for example, a shaft, so that as the shaft moves linearly or rotates, it is possible for the multi-bladed part 150 to form the cog 11 on the biodegradable thread 10.

According to the present invention, as schematically shown in FIGS. 2 and 3, the multi-bladed part 150 has two blades arranged up and down. In specific, the multi-bladed part 150 includes a first blade member 151 and a second blade member 155 located above the first blade member 151 for forming the two peaks 12 and 13 along a longitudinal direction of the biodegradable thread 10 and a connection member 157 disposed between the first blade member 151 and the second blade member 155.

Referring to FIG. 3, the first blade member 151 and the second blade member 155 are arranged in parallel with each other by means of the connection member 157, and so as to allow a portion of the cog 11 to be separated to form the two peaks 12 and 13, the first blade member 151 is located in front of the second blade member 155 located thereabove.

Even though not shown, a guide member is disposed on top of the connection member 157 to allow the second blade member 155 to linearly move with respect to the connection member 157, and in the same manner as above, another guide member is disposed on the underside of the connection member 157 to allow the first blade member 151 to linearly move with respect to the connection member 157.

Accordingly, the second blade member 155 with respect to the first blade member 151 is adjusted in position. That is, the front end portion of the second blade member 155 with respect to the front end portion of the first blade member 151 is adjusted in position.

As a result, an inclination angle of the multi-bladed part 150 with respect to the biodegradable thread 10 may be varied according to the shape of the cog 11 to be formed, and in this case, the second blade member 155 with respect to the first blade member 151 is adjusted in position, so that the cog 11 having a desired shape may be formed by means of the second blade member 155 as well as the first blade member 151.

Further, the first blade member 151 and the second blade member 155 are detachably attached to the connection member 157, and if the blade members are worn out or damaged, accordingly, it is easy to perform their repairing or exchanging work.

As shown in FIG. 3, the front edges of the first blade member 151 and the second blade member 155 are inclined upwardly toward the backward directions thereof, but the edge shapes of the blade members may be freely determined according to the desired shape of the cog 11. For example, the front edges of the first blade member 151 and the second blade member 155 may be inclined downwardly toward the backward directions thereof. That is, the front edges of the first blade member 151 and the second blade member 155 may be not limited in shape.

Further, the multi-bladed part 150 has the two blade members 151 and 155, but of course, it may have three or more blades. So as to more improve the rapidness and effectiveness in forming the cogs 11, a third blade member may be located by connecting another connection member to top of the second blade member 155 as shown in FIG. 3.

Now, an explanation of a biodegradable thread manufacturing method according to an embodiment of the present invention will be given with reference to FIG. 4.

Figure 4:
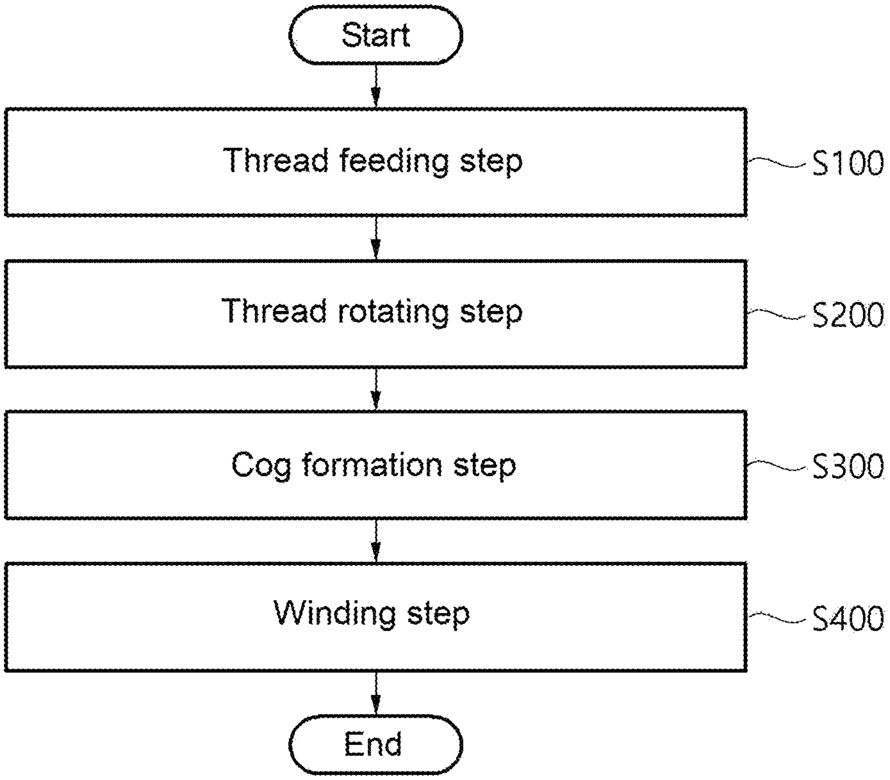
FIG. 4 is a flow chart showing a biodegradable thread manufacturing method according to an embodiment of the present invention.

FIG. 4 is a flow chart showing a biodegradable thread manufacturing method according to an embodiment of the present invention.

As shown, a biodegradable thread manufacturing method according to the present invention includes the step of feeding the biodegradable thread 10 from the thread feeding unit 110 (at step S100), rotating the biodegradable thread 10 by the set angle through the thread rotating unit 120 (at step S200), forming the cog 11 with the two or more peaks 12 and 13 on the biodegradable thread 10 through the one-time operation of the multi-bladed part 150 of the cog formation unit 140 (at step S300), and winding the biodegradable thread 10 through the winding unit 170 (at step S400).

As mentioned above, the biodegradable thread 10 as the raw material is fed at the thread feeding step S100 according to the present invention, and the biodegradable thread 10 fed rotates by the set angle, for example, by 45° in one direction (clockwise or counterclockwise direction) at the thread rotating step S200 according to the present invention. After that, the cogs 11 are formed on the rotating biodegradable thread 10 at the cog formation step S300. As a result, as shown in FIG. 1, the cogs 11 are formed on the biodegradable thread 10 at intervals of 45° in the spiral direction of the biodegradable thread 10.

Because the multi-bladed part 150 of the cog formation unit 140 includes the two blades, that is, the first blade member 151 and the second blade member 155, at the cog formation step S300, the cog 11 with the two peaks 12 and 13 whose ends are separated from each other is formed on the biodegradable thread 10 through the one-time operation of the first blade member 151 and the second blade member 155.

At the thread winding step S400, further, the biodegradable thread 10 on which the cogs 11 are formed is wound through the winding unit 170 and then kept in given place.

According to the present invention, therefore, the cog 11 with the two peaks 12 and 13 is formed on the biodegradable thread 10 through the one-time operation of the cog formation unit 140, thereby improving the production efficiency of the biodegradable thread, and if the biodegradable thread 10, which includes the cogs 11 each having the peaks 12 and 13 formed to the set shape, is applied to the patient's skin, a coupling force of the biodegradable thread 10 with the skin tissues is enhanced, thereby obtaining great effectiveness in his or her skin lifting.

Now, explanations of another example of the multi-bladed part of the cog formation unit according to the present invention will be given below, but the description on the members corresponding to the multi-bladed part as mentioned above will be omitted.

Figure 5:
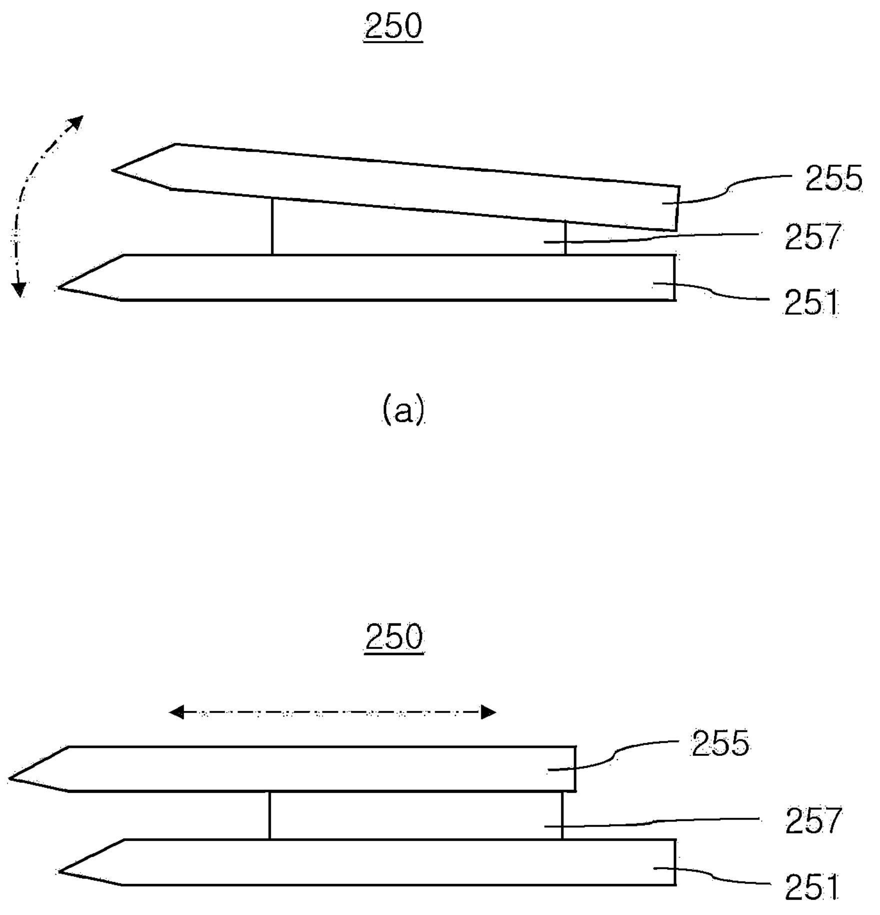
FIG. 5 illustrates side views showing another example of the multi-bladed part according to the present invention.
Figure 6:
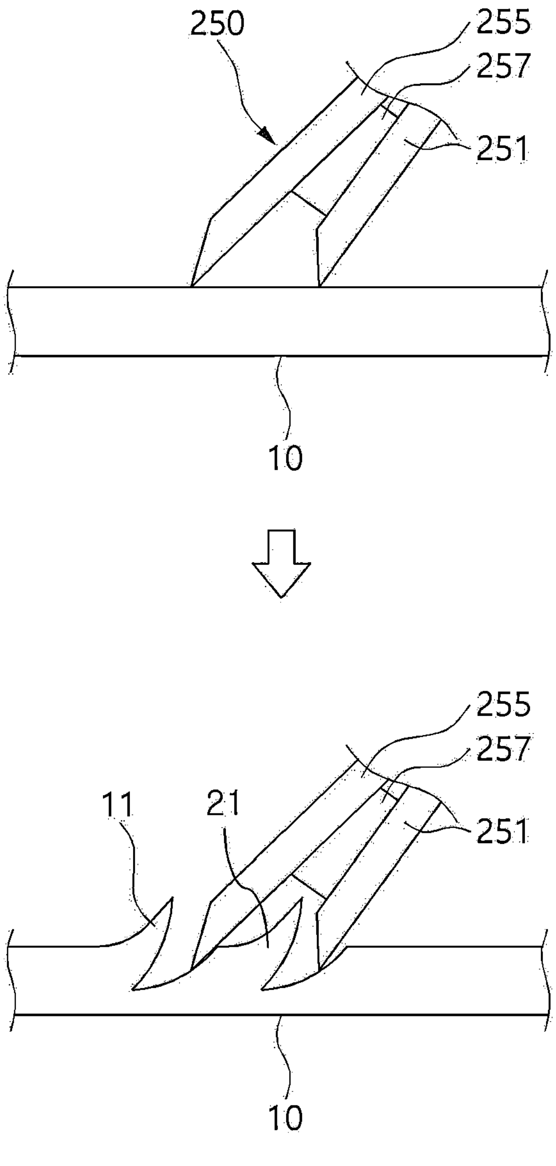
FIG. 6 is a side view showing an operation of the multi-bladed part of FIGS. 5*a* and 5*b*.

FIGS. 5*a* and 5*b* are side views showing another example of the multi-bladed part according to the present invention, and FIG. 6 is a side view showing an operation of the multi-bladed part of FIGS. 5*a* and 5*b*.

Referring to FIG. 5*a*, a multi-bladed part 250 of the cog formation unit according to the present invention includes a first blade member 251, a second blade member 255, and an inclination adjustment member 257 located between the first blade member 251 and the second blade member 255.

For example, the second blade member 255 is inclinedly located with respect to the first blade member 251 so that a space between the first blade member 251 and the second blade member 255 becomes narrow as it goes front to back, and in this case, an angle of inclination of the second blade member 255 with respect to the first blade member 251 is adjusted by means of the inclination adjustment member 257.

Even though not shown in detail, according to the present invention, the inclination adjustment member 257 has a structure of a hinge to thus adjust the angle of inclination of the second blade member 255 with respect to the first blade member 251, and further, the inclination adjustment member 257 has a fastening portion (not shown) formed thereon to thus allow the second blade member 255 to be firmly fixed thereto after the angle of inclination of the second blade member 255 with respect to the first blade member 251 has been adjusted.

Referring to FIG. 5*b*, further, the multi-bladed part 250 of the cog formation unit according to the present invention includes a guide member (not shown) disposed on the inclination adjustment member 257 to linearly move at least one of the first blade member 251 and the second blade member 255 so that the front end portion of the second blade member 255 with respect to the first blade member 251 is adjusted in position.

As mentioned above, the distance between the front end portions of the first blade member 251 and the second blade member 255 is adjusted by means of the inclination adjustment member 257 and the guide member, thereby allowing the intervals, depths, and shapes of the cogs 11 to be varied.

For example, as shown in FIG. 6, the angle of inclination between the first blade member 251 and the second blade member 255 is adjusted, and otherwise, the front end portion of the second blade member 255 is located in front of the first blade member 251, so that the cog 11 having two or more peaks is formed on the outer peripheral surface of the biodegradable thread 10 through the one-time operation of the multi-bladed part 250.

According to another embodiment of the present invention, in the biodegradable thread having a plurality of cogs formed on the outer peripheral surface, each of the cogs has two or more peaks whose end portions are separated from each other, and the peaks may be separated left and right based on a longitudinal direction of the biodegradable thread.

Figure 7:
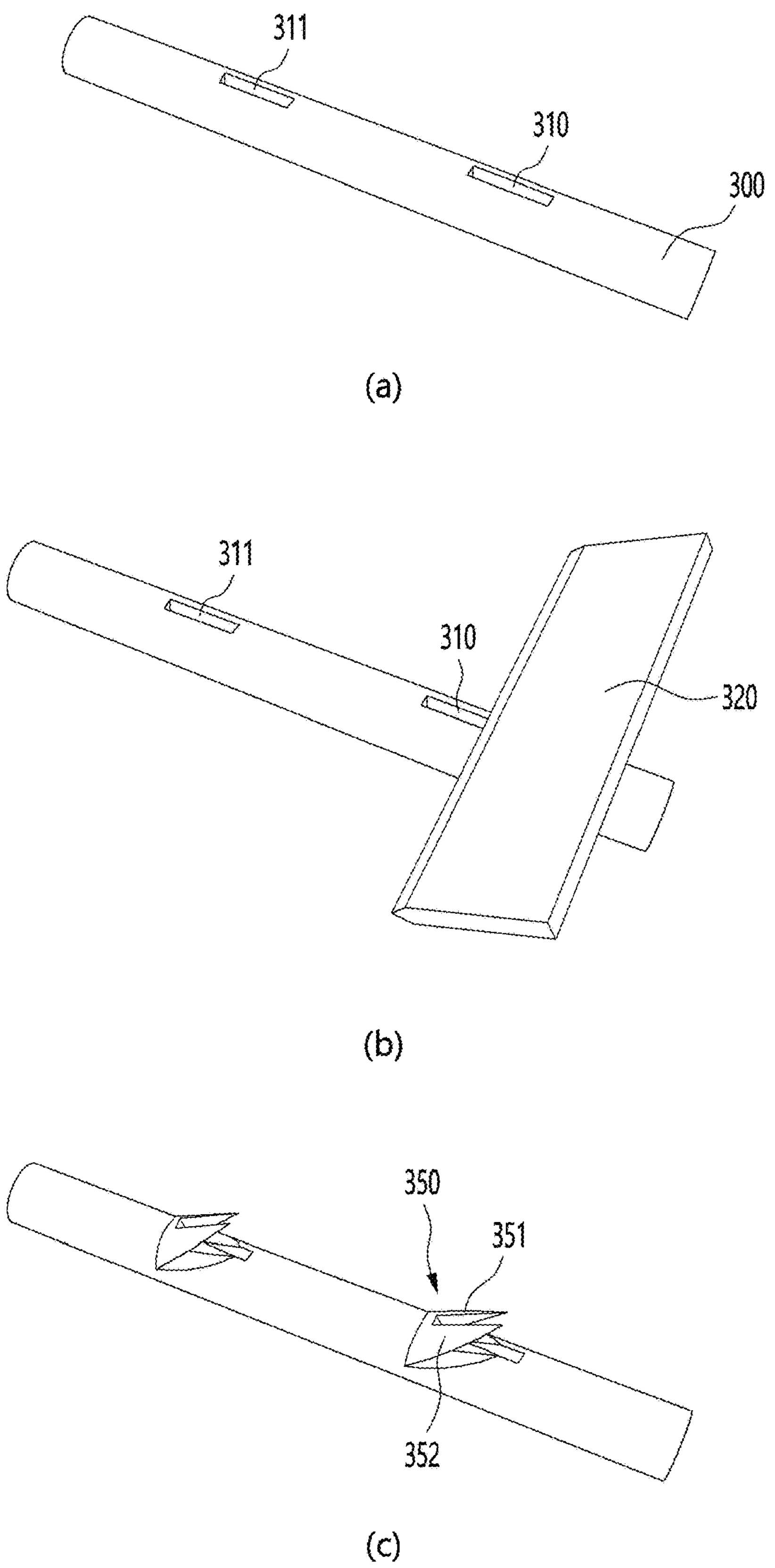
FIG. 7 illustrates perspective views showing a biodegradable thread manufacturing method according to another embodiment of the present invention.

FIGS. 7*a* to 7*c* are perspective views showing a biodegradable thread manufacturing method according to another embodiment of the present invention, and in this case, the description on the same parts as mentioned in FIGS. 1 and 2 will be omitted.

Referring first to FIG. 7*a*, slots 310 and 311 are formed on the outer peripheral surface of the biodegradable thread 300 in the longitudinal direction of the biodegradable thread 300.

By each of the slots 310 and 311 formed in the longitudinal direction of the biodegradable thread 300, a portion the outer peripheral surface of the biodegradable thread 300 may be separated left and right based on a longitudinal direction.

As shown in FIG. 7*b*, after that, the biodegradable thread 300 is cut by a given depth in a direction crossing the slot 310 formed thereon through a blade 320, thereby forming a cog on the biodegradable thread 300.

Figure 8:
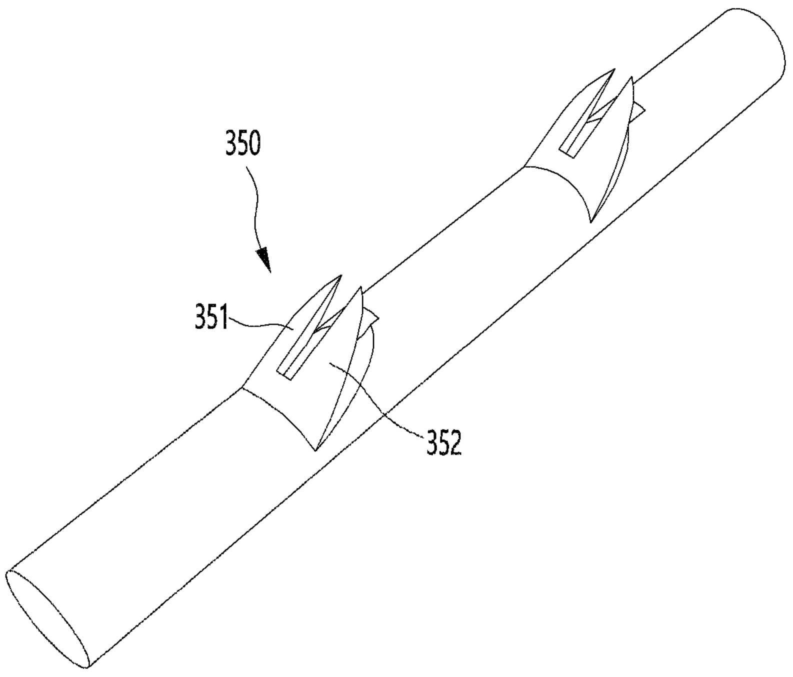
FIG. 8 is a perspective view showing another structure of the biodegradable thread according to the present invention.

Next, as shown in FIGS. 7*c* and 8, a cog 350 having two peaks 351 and 352 whose end portions are separated from each other is formed on the biodegradable thread 300, and the peaks 351 and 352 are separated left and right based on the longitudinal direction of the biodegradable thread 300 by the slots 310 and 311 formed in the longitudinal direction of the biodegradable thread 300.

Figure 9:
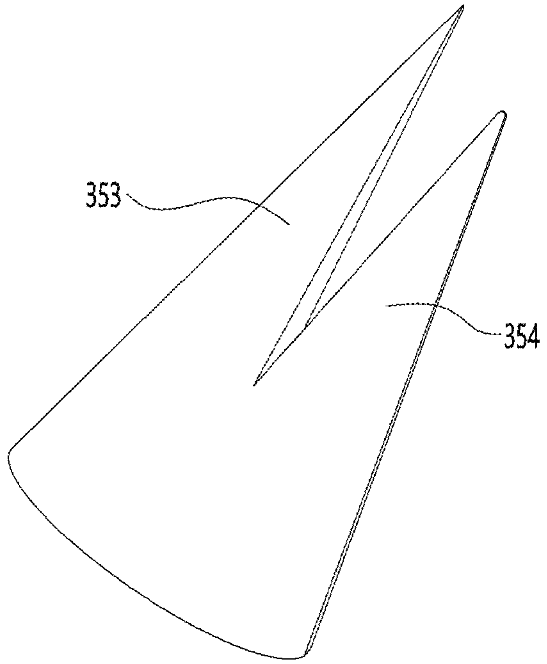
FIG. 9 illustrates perspective views showing other examples of the cog formed on the biodegradable thread.
Figure 9:
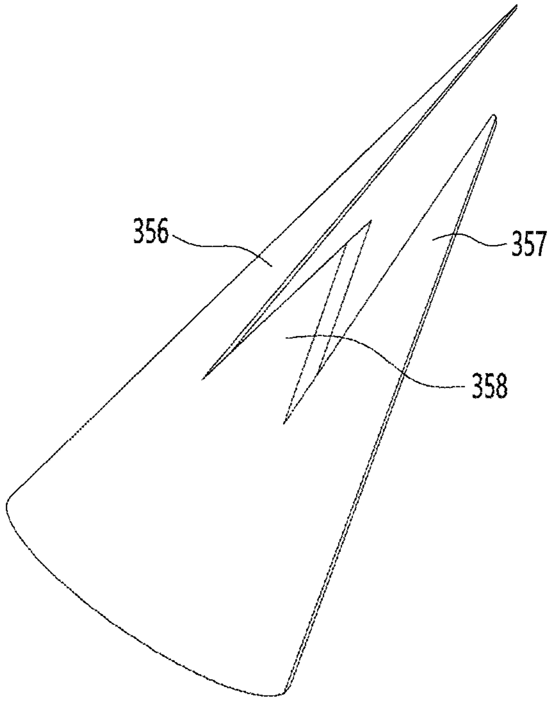

FIGS. 9*a* and 9*b* are perspective views showing other examples of the cog formed on the biodegradable thread according to the present invention. As shown in FIG. 9*a*, peaks 353 and 354 of the cog have different sizes from each other, and otherwise, as shown in FIG. 9*b*, three or more peaks 356 to 358 are formed on the cog.

Figure 10:
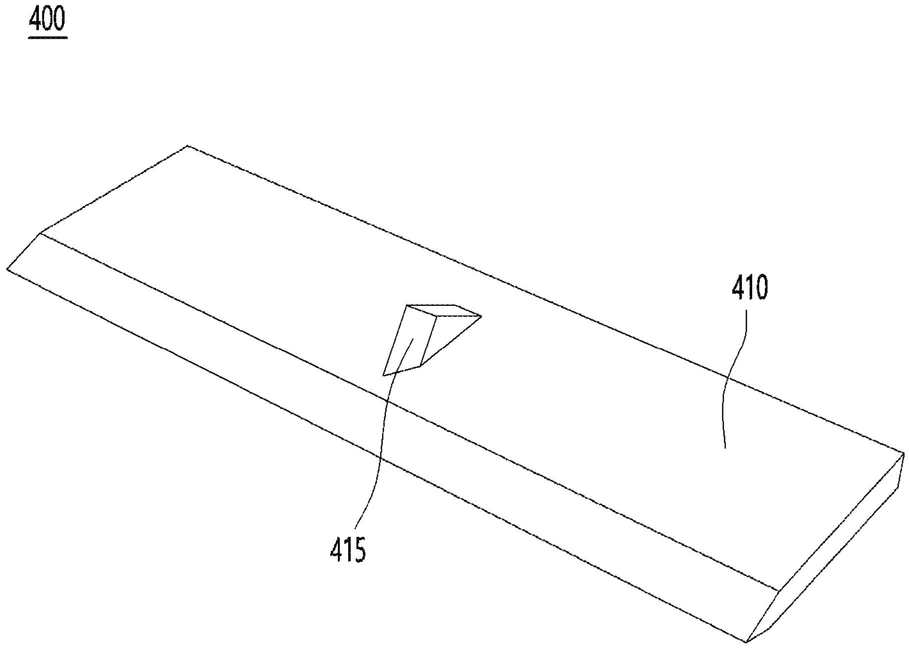
FIG. 10 is a perspective view showing yet another example of the multi-bladed part according to the present invention.

FIG. 10 is a perspective view showing yet another example of the multi-bladed part according to the present invention.

Referring to FIG. 10, a multi-bladed part 400 according to the present invention includes a first blade member 410 and a second blade member 415 disposed on top of the first blade member 410 in a direction crossing the first blade member 410.

Figure 11:
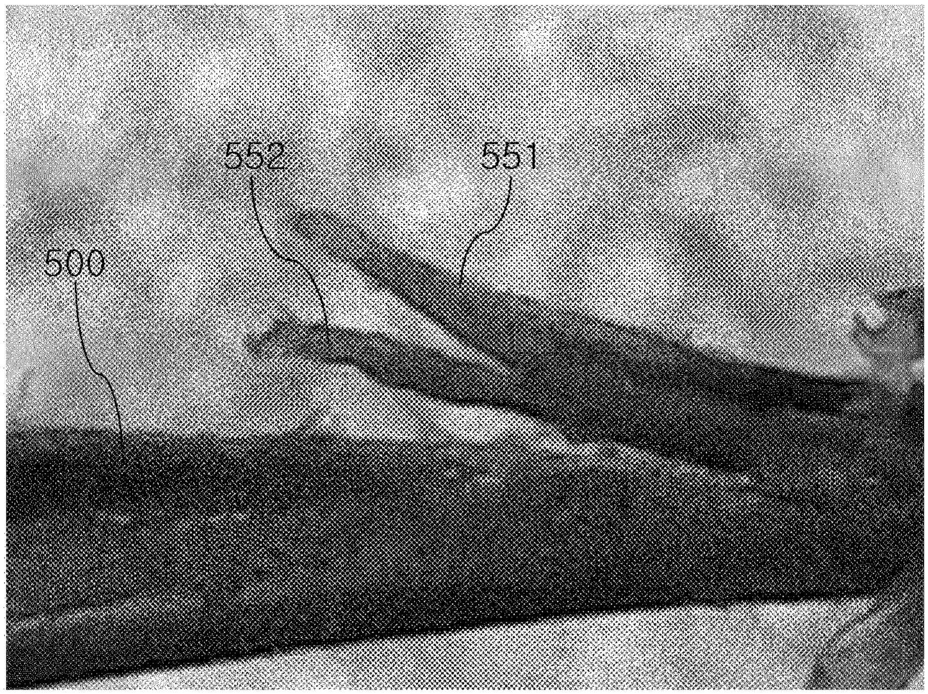
FIG. 11 is an enlarged photograph showing the cog of the biodegradable thread manufactured according to the present invention.

As shown in FIG. 10, the outer peripheral surface of the biodegradable thread is cut by using the first and second blade members 410 and 415 arranged to cross each other, so that through the one-time operation of the multi-bladed part 400, the cog having two or more peaks 551 and 552 is formed on a biodegradable thread 500 (See FIG. 11).

On the other hand, when the multi-bladed part 400 cuts the outer peripheral surface of the biodegradable thread, the second blade member 415 cuts the outer peripheral surface of the biodegradable thread in the longitudinal direction. Accordingly, as described with reference to FIGS. 8 and 9, a plurality of peaks may have a structure separated left and right based on the longitudinal direction of the biodegradable thread.

FIG. 11 is an enlarged photograph showing the cog of the biodegradable thread manufactured according to the present invention. Through the biodegradable thread manufacturing apparatus as mentioned above, the cog having two or more peaks is formed on the outer peripheral surface of the biodegradable thread.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

The invention claimed is:

1. A biodegradable thread having a plurality of cogs formed on an outer peripheral surface, wherein:

the plurality of cogs each have two or more peaks whose end portions are separated from each other, the two or more peaks are separated left and right based on a longitudinal direction of the biodegradable thread, and the biodegradable thread has a resected region formed by cutting into a body of the biodegradable thread, and at least one of the plurality of cogs is defined across the resected region.

2. The biodegradable thread according to claim 1, wherein at least two of the two or more peaks have different sizes or shapes.

* * * * *